US009339199B2

(12) United States Patent
Yu et al.

(10) Patent No.: US 9,339,199 B2
(45) Date of Patent: May 17, 2016

(54) PHYSIOLOGICAL SIGNAL DETECTION DEVICE

(71) Applicant: Quanta Computer Inc., Kuei Shan Hsiang, Tao Yuan Shien (TW)

(72) Inventors: Chih-Hsiung Yu, Tao Yuan Shien (TW); Yung-Ming Chung, Tao Yuan Shien (TW); Chih-Hsiung Chang, Tao Yuan Shien (TW)

(73) Assignee: QUANTA COMPUTER INC., Guishan Dist., Taoyuan (TW)

( * ) Notice: Subject to any disclaimer, the term of this patent is extended or adjusted under 35 U.S.C. 154(b) by 81 days.

(21) Appl. No.: 13/777,533

(22) Filed: Feb. 26, 2013

(65) Prior Publication Data
US 2014/0100468 A1 Apr. 10, 2014

(30) Foreign Application Priority Data

Oct. 9, 2012 (TW) .............................. 101137215 A

(51) Int. Cl.
*A61B 5/0452* (2006.01)
*A61B 5/024* (2006.01)
*A61B 5/00* (2006.01)

(52) U.S. Cl.
CPC ........... *A61B 5/02444* (2013.01); *A61B 5/0002* (2013.01); *A61B 2560/0214* (2013.01)

(58) Field of Classification Search
CPC ............. A61B 5/02; A61B 2560/0204; A61B 2560/0209; A61B 2560/0214; A61B 2560/0266; A61B 2560/029; A61B 5/0402; A61B 5/0452
USPC ................................ 600/513–515; 607/33, 34
See application file for complete search history.

(56) References Cited

U.S. PATENT DOCUMENTS

| 5,333,615 A | * | 8/1994 | Craelius | ............. | A61B 5/04325 600/509 |
| 5,882,300 A | * | 3/1999 | Malinouskas | ........ | A61B 5/4356 128/903 |
| 2008/0027679 A1 | * | 1/2008 | Shklarski | ............. | A61B 5/0022 702/182 |

(Continued)

FOREIGN PATENT DOCUMENTS

TW M415690 11/2011

OTHER PUBLICATIONS

Taiwanese language office action dated Oct. 8, 2014.

(Continued)

*Primary Examiner* — Michael Kahelin
*Assistant Examiner* — Minh Duc Pham
(74) *Attorney, Agent, or Firm* — McClure, Qualey & Rodack, LLP

(57) ABSTRACT

A physiological signal detection device has a battery disposed in the physiological signal detection device, a first input terminal, a second input terminal, and a charging detection terminal A physiological signal detection circuit generates a physiological signal according to a detection result of the first input terminal and the second input terminal A charging control circuit is electrically coupled to the first input terminal, the second input terminal and the charging detection terminal, wherein, when the first input terminal and the second input terminal are coupled to a power supply supplied by a charging device, the charging detection terminal receives a charging indication signal of the charging device and according to the charging indication signal the charging device is enabled so as to charge the battery with the power supply.

9 Claims, 4 Drawing Sheets

(56) References Cited

U.S. PATENT DOCUMENTS

| | | | |
|---|---|---|---|
| 2009/0157146 A1* | 6/2009 | Linder | A61N 1/37217 607/60 |
| 2010/0114216 A1* | 5/2010 | Krause | A61N 1/3787 607/5 |
| 2011/0208076 A1* | 8/2011 | Fong | A61B 5/0006 600/509 |
| 2013/0116520 A1* | 5/2013 | Roham | A61B 5/6833 600/324 |

OTHER PUBLICATIONS

English language translation of abstract of TW M415690 (published Nov. 11, 2011).

* cited by examiner

PHYSIOLOGICAL SIGNAL DETECTION DEVICE

CROSS REFERENCE TO RELATED APPLICATIONS

This Application claims priority of Taiwan Patent Application No. 101137215 filed on Oct. 9, 2012, the entirety of which is incorporated by reference herein.

BACKGROUND OF THE INVENTION

1. Field of the Invention

The present invention relates to a signal detection device, and in particular, relates to a physiological signal detection device.

2. Description of the Related Art

Healthcare for the elderly, long-distanced healthcare and personal healthcare have attracted great attention recently. Therefore, portable electronic products have been developed for monitoring the health of people. Design of these electronic products emphasizes the characteristics of portability, power-saving, and low price. Also, these electronic products have the capability of tracking physiological signals, such as temperature, electrocardiogram, and pulse information of users, to effectively record the physiology of the users. Thus, a physiological signal detection device that is easy to operate, has a compact structure, and is convenient for charging and storing is in need.

BRIEF SUMMARY OF THE INVENTION

A physiological signal detection device comprises a battery disposed in the physiological signal detection device, comprising a positive terminal and a negative terminal, a first input terminal, a second input terminal, and a charging detection terminal. A physiological signal detection circuit is electrically coupled to the first input terminal and the second input terminal, wherein, when the first input terminal and the second input terminal are electrically connected to a measure target, the physiological signal detection circuit generates a physiological signal according to a detection result of the first input terminal and the second input terminal A charging control circuit is electrically coupled to the first input terminal, the second input terminal and the charging detection terminal, wherein, when the first input terminal and the second input terminal are coupled to a power supply supplied by a charging device, the charging detection terminal receives a charging indication signal of the charging device and according to the charging indication signal the charging device is enabled so as to charge the battery with the power supply.

The invention further discloses a charging device, wherein the charging device comprises a first output terminal, a charging indication terminal, and a second output terminal, respectively, coupled to the first input terminal, the charging detection terminal and the second input terminal A charging circuit is coupled to the first terminal, the second terminal and the third terminal so as to supply the power supply and the charging indication signal.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
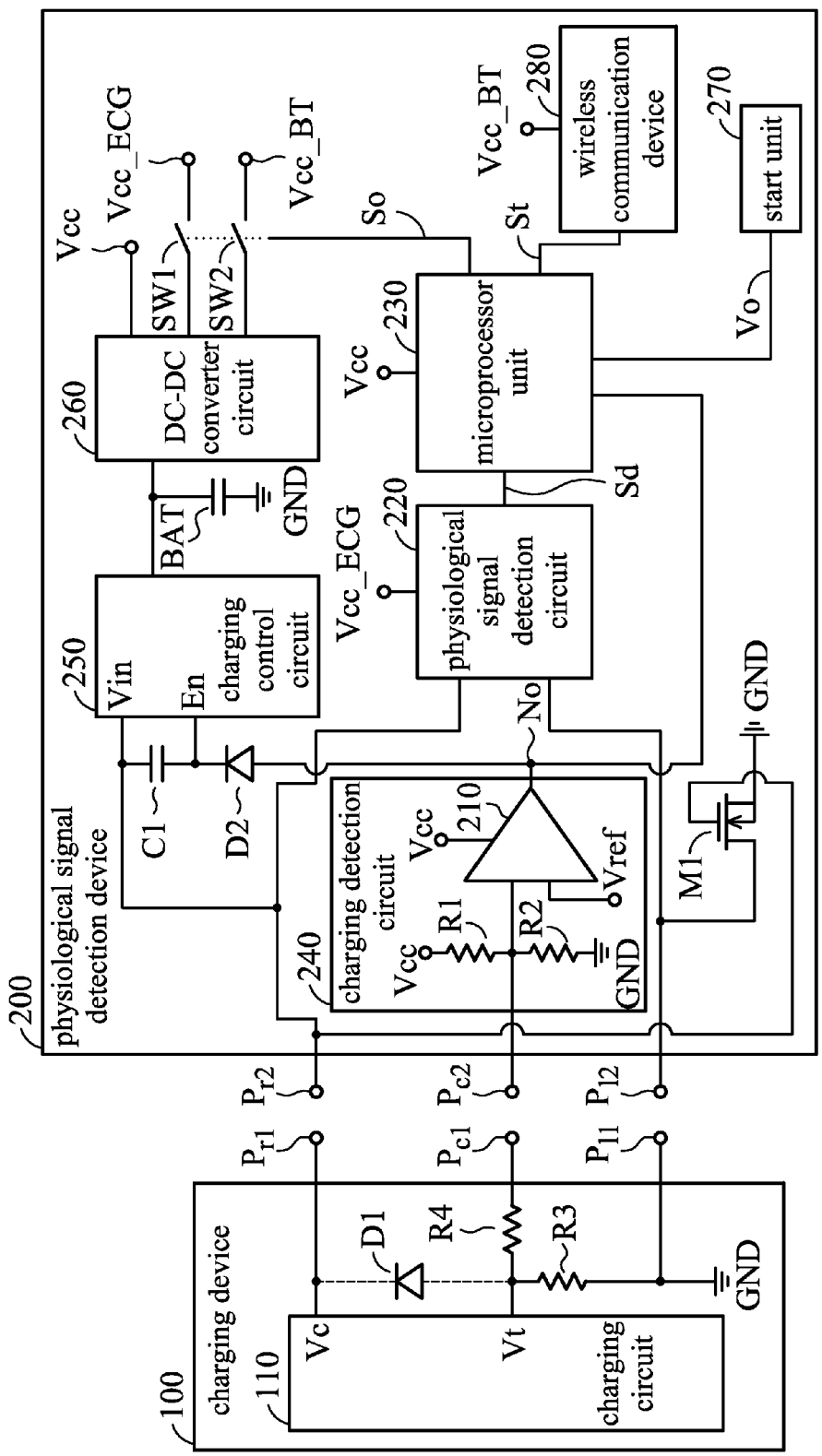
FIG. 1 is a schematic diagram for illustrating a physiological signal detection device and a charging device according to an embodiment of the invention.

FIG. 1 is a schematic diagram for illustrating a physiological signal detection device 200 and a charging device 100 according to an embodiment of the invention. In the embodiment of the invention, the physiological signal detection device 200 is an electrocardiogram measure device and is portable by using a magnet to fix the physiological signal detection device 200 to the clothes of a user. The physiological signal detection device 200 has three terminals to connect with outer connection terminals. The three terminals are a first input terminal $P_{r2}$, a second input terminal $P_{l2}$ and a charging detection terminal $P_{c2}$. The feature of the invention is that the first input terminal $P_{r2}$ and the second input terminal $P_{l2}$ are not only the input terminals of an electro-cardio signal of a human body under a measuring operation mode, but also the input terminals for receiving a power supply of the charging device 100 in conjunction with the charging detection terminal $P_{c2}$ under a charging mode.

When the physiological signal detection device 200 connects to the charging device 100, the first input terminal $P_{r2}$, the charging detection terminal $P_{c2}$ and the second input terminal $P_{l2}$ are connected to a first output terminal $P_{r1}$, a charging indication terminal $P_{c1}$ and a second output terminal $P_{l1}$ of the charging device 100, respectively. The physiological signal detection device 200 receives the power supply of a charging circuit 110 by the first input terminal $P_{r2}$ and the second input terminal $P_{l2}$ and receives a charging indication signal Vt by the charging detection terminal $P_{c2}$.

Referring to FIG. 1, the physiological signal detection device 200 has a charging detection circuit 240 coupled to the charging detection terminal $P_{c2}$ so as to detect the voltage of the charging detection terminal $P_{c2}$, determine the charging indication signal Vt and further output a corresponding detection signal to control an operation mode of the physiological signal detection device 200. For example, the charging detection circuit 240 is composed of a comparator 210, a resistor R1 and a resistor R2. When the voltage of the charging detection terminal $P_{c2}$ is lager than a reference voltage Vref, the charging detection circuit 240 outputs a corresponding first detection signal to a node No so as to correspondingly indicate the physiological signal detection device 200 under a charging/storage mode. When the voltage of the charging detection terminal $P_{c2}$ is not lager than the reference voltage Vref, the charging detection circuit 240 outputs a corresponding second detection signal to the node No so as to correspondingly indicate the physiological signal detection device 200 under a measuring operation mode.

The physiological signal detection device 200 has a physiological signal detection circuit 220 that is electrically connected to the first input terminal $P_{r2}$ and the second input terminal $P_{l2}$. The physiological signal detection circuit 220 is driven by the power supply Vcc_ECG, receiving, and processing the input signals of the first input terminal $P_{r2}$ and the second input terminal $P_{l2}$, such as the signal of bioelectricity, and transforming the input signals into a physiological signal Sd as an output.

The physiological signal detection device 200 has a microprocessor unit 230 coupled to the physiological signal detection circuit 220 and the node No. The microprocessor unit 230 is driven by a power supply Vcc. When receiving the second detection signal from the node No, the microprocessor unit 230 receives, and processes the physiological signal Sd from the physiological signal detection circuit 220 and calculates a plurality of a physiological information St according to the physiological signal Sd. In some embodiments, the physiological information may include a heart rate, calorie consumption, an electrocardiogram, and an exercise time. The physiological signal detection device 200 further has a wireless communication device 280 so as to transmit the physiological information St to a personal computer, a cloud storage and a portable device for storing and displaying.

The physiological signal detection device 200 has a battery BAT and a charging control circuit 250. The battery BAT has a positive terminal and a negative terminal and is disposed inside the physiological signal detection device 200 to provide the power supply to inner circuits of the physiological signal detection device 200. The charging control circuit 250 has a power input terminal Vin and a control terminal EN coupled to the first input terminal $P_{r2}$ and the node No, respectively. When the control terminal EN receives the first detection signal from the node No (i.e., under the charging/storage mode), the charging control circuit 250 is enabled and processes a power supply input from the first input terminal $P_{r2}$ via the input terminal Vin and provides the processed power to the positive terminal of the battery BAT. When the node No outputs the second detection signal (i.e., under the measuring operation mode), the charging control circuit 250 is disabled, cuts off the connection between the power input terminal Vin and the battery BAT and stops charging the battery BAT. The physiological signal detection device 200 further has a transistor M1, wherein the drain electrode of the transistor M1 is coupled to the second input terminal $P_{l2}$, the gate electrode of the transistor M1 is coupled to the first input terminal $P_{r2}$, and the source electrode and body electrode of the transistor M1 are connected to the negative terminal of the battery BAT and a ground via a reference voltage node GND. The battery BAT is charged via the first input terminal $P_{r2}$ and the second input terminal $P_{l2}$. The physiological signal detection device 200 further has a capacitor C1 coupled between the power input terminal Vin and the control terminal EN and a diode D2 coupled between the node No and the control terminal EN.

The physiological signal detection device 200 has a DC-DC converter circuit 260 and switches SW1, SW2. The DC-DC converter circuit 260 is coupled to the battery BAT and transforms the voltage supplied from the battery BAT into power supplies for circuits, wherein the power supplies provided to the microprocessor unit 230, the physiological signal detection circuit 220 and the wireless communication device 280 are Vcc, Vcc_ECG and Vcc_BT, respectively. Two terminals of the switch SW1 are respectively connected to the physiological signal detection circuit 220 and the terminal of the power supply Vcc_ECG outputted from the DC-DC converter circuit 260. The control terminal of the switch SW1 is connected to the microprocessor unit 230 and when the microprocessor unit 230 receives the second detection signal from the node No (i.e., under the measuring operation mode), the microprocessor unit 230 correspondingly generates a control signal So that has a first voltage level and turns on the switch SW1 to provide the power supply Vcc_ECG to the physiological signal detection circuit 220. When the microprocessor unit 230 receives the first detection signal from the node No (i.e., under the charging/storage mode), the microprocessor unit 230 correspondingly generates the control signal So that has a second voltage level and turns off the switch SW1 so that the power supply Vcc_ECG does not be provided to the physiological signal detection circuit 220. Two terminals of the switch SW2 are respectively connected to the wireless communication device 280 and the terminal of a power supply Vcc_BT outputted from the DC-DC converter circuit 260. The control terminal of the switch SW2 is connected to the microprocessor unit 230 and when the microprocessor unit 230 receives the second detection signal from the node No (i.e., under the measuring operation mode), the microprocessor unit 230 correspondingly generates a control signal So that has the first voltage level and turns on the switch SW2 to provide the power supply Vcc_BT to the wireless communication device 280. When the microprocessor unit 230 receives the first detection signal from the node No (i.e., under the charging/storage mode), the microprocessor unit 230 correspondingly generates the control signal So that has the second voltage level and turns off the switch SW2 so that the power supply Vcc_BT does not be supplied to the wireless communication device 280.

The physiological signal detection device 200 has a start unit 270 and is coupled to the microprocessor unit 230 so as to generate a start instruction Vo. When the start instruction Vo is transmitted to the microprocessor unit 230, the physiological signal detection device 200 operates in the measuring operation mode. The microprocessor unit 230 further turns on the switch SW1 and/or SW2 so that the battery BAT provides the power supply to the physiological signal detection circuit 220 and/or the wireless communication device 280 to start the physiological signal detection device 200 to detect the signal of bioelectricity. In one embodiment, the start unit 270 can be a Hall sensor. When the physiological signal detection device 200 is combined with a magnet on a user, the Hall sensor transmits the start instruction Vo due to the variations of the magnetic field so that the physiological signal detection circuit 220 of the physiological signal detection device 200 performs measuring.

The charging device 100 can be used with the physiological signal detection device 200 so as to charge the physiological signal detection device 200. The charging device 100 has three terminals: a first output terminal $P_{r1}$, a second output terminal $P_{l1}$ and a charging indication terminal $P_{c1}$ that corresponds to the first input terminal $P_{r2}$, the second input terminal $P_{l2}$ and the charging detection terminal $P_{c2}$ of the physiological signal detection device 200. When the charging device 100 is combined with the physiological signal detection device 200, the charging device 100 inputs a voltage Vc to the first input terminal $P_{r2}$ via the first output terminal $P_{r1}$, inputting a voltage Vt (the charging indication signal) to the charging detection terminal $P_{c2}$ via the charging indication terminal $P_{c1}$, and connecting the second input terminal $P_{l2}$ with the reference voltage node GND via the second output terminal $P_{l1}$. The charging device 100 further has a diode D1 that is coupled between the first output terminal $P_{r1}$ and the output terminal of the voltage Vt, a resistor R4 that is coupled between the output terminal of the voltage Vt and the charging indication terminal $P_{c1}$, and a resistor R3 that is coupled between the output terminal of the voltage Vt and the second output terminal $P_{t1}$.

Figure 2:
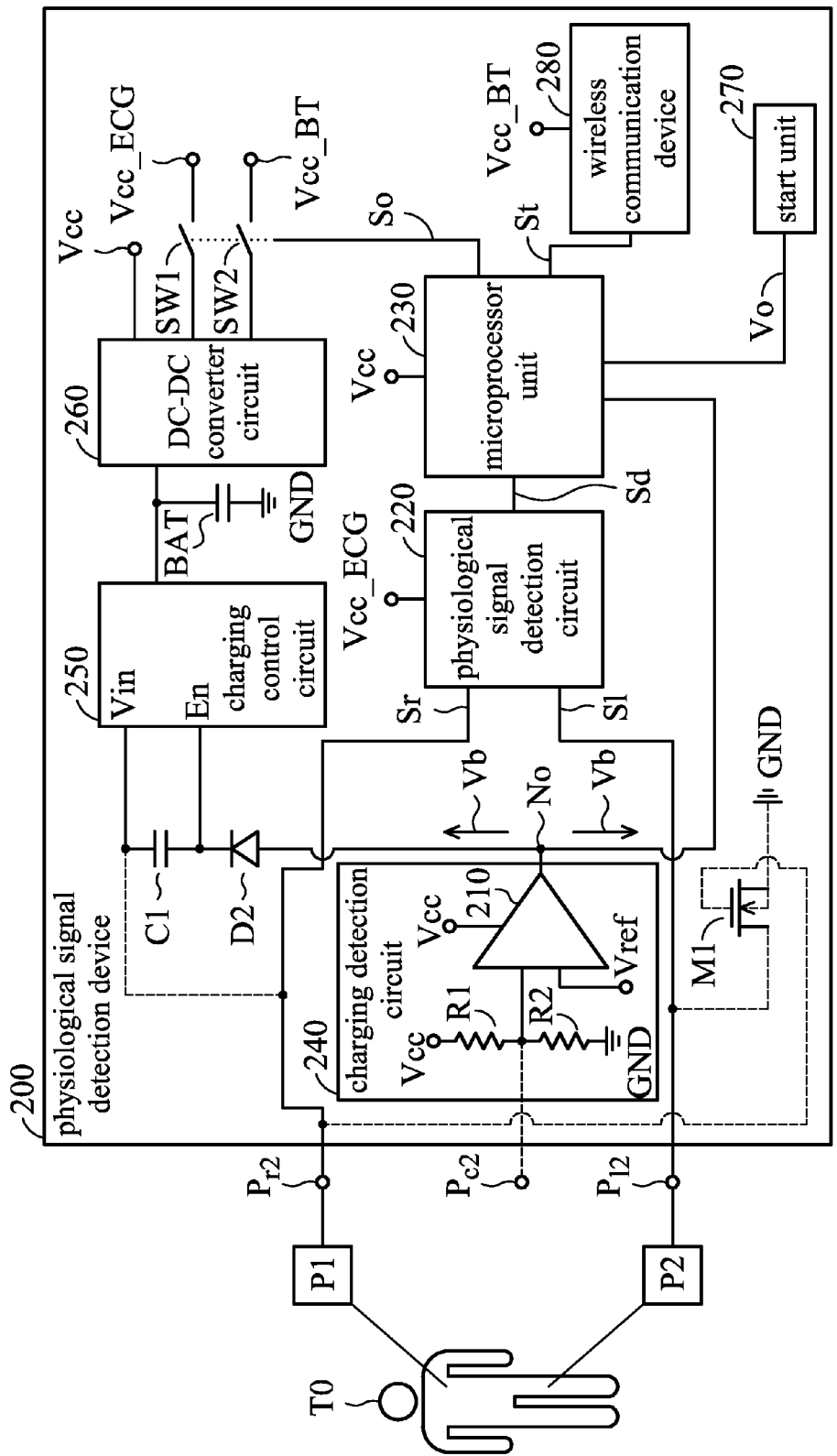
FIG. 2 is a circuit diagram for illustrating the embodiment, when the physiological signal detection device 200 is operating in the measuring operation mode of FIG. 1.

FIG. 2 is a circuit diagram for illustrating the embodiment, when the physiological signal detection device 200 is operating in the measuring operation mode of FIG. 1. The first input terminal $P_{r2}$ and the second input terminal $P_{t2}$ are respectively connected to connection pads P1 and P2 and the connection pads P1 and P2 are respectively connected to two terminal of a measure target T0, such as a human body, wherein the charging detection terminal $P_{c2}$ is floating. When the voltage level of the charging detection terminal $P_{c2}$ is a first state (i.e. 2.6V), after the comparator 210 compares the voltage level of the charging detection terminal $P_{c2}$ with the reference voltage Vref (i.e. 2.8V), the charging detection circuit 240 outputs a corresponding second detection signal Vb to the node No so as to correspondingly indicate the physiological signal detection device 200 operating in the measuring operation mode.

When the microprocessor unit 230 receives the second detection signal Vb from the node No, the microprocessor unit 230 correspondingly generates the control signal So that has the first voltage level so as to turn on the switch SW2 to provide the power supply Vcc_BT to the wireless communication device 280 and turn on the switch SW1 to provide the power supply Vcc_ECG to the physiological signal detection circuit 220.

When the user starts to perform measuring, the start unit 270 generates the start instruction Vo to the microprocessor unit 230 so that the physiological signal detection device 200 performs detecting. The physiological signal detection circuit 220 of the physiological signal detection device 200 measures the signal of bioelectricity of the target T0, such as the electrocardio signal, via connection pads P1 and P2 and transforms the measure results into the physiological signal Sd.

When the second detection signal Vb from the node No is received, the microprocessor unit 230 receives and processes the physiological signal Sd from the physiological signal detection circuit 220 for calculating the physiological information St according to the physiological signal Sd. The physiological information St is uploaded to the personal computer, the cloud storage and the portable device for storing and displaying.

Due to the second detection signal Vb outputted from the node No, the charging control circuit 250 is disabled so as to cut off the connections between the power input terminal Vin and the battery BAT to stop charging the battery BAT. Because the transistor M1 operates in the turn-off state, the second input terminal $P_{t2}$ is electrically isolated from the negative terminal of the battery BAT.

Figure 3:
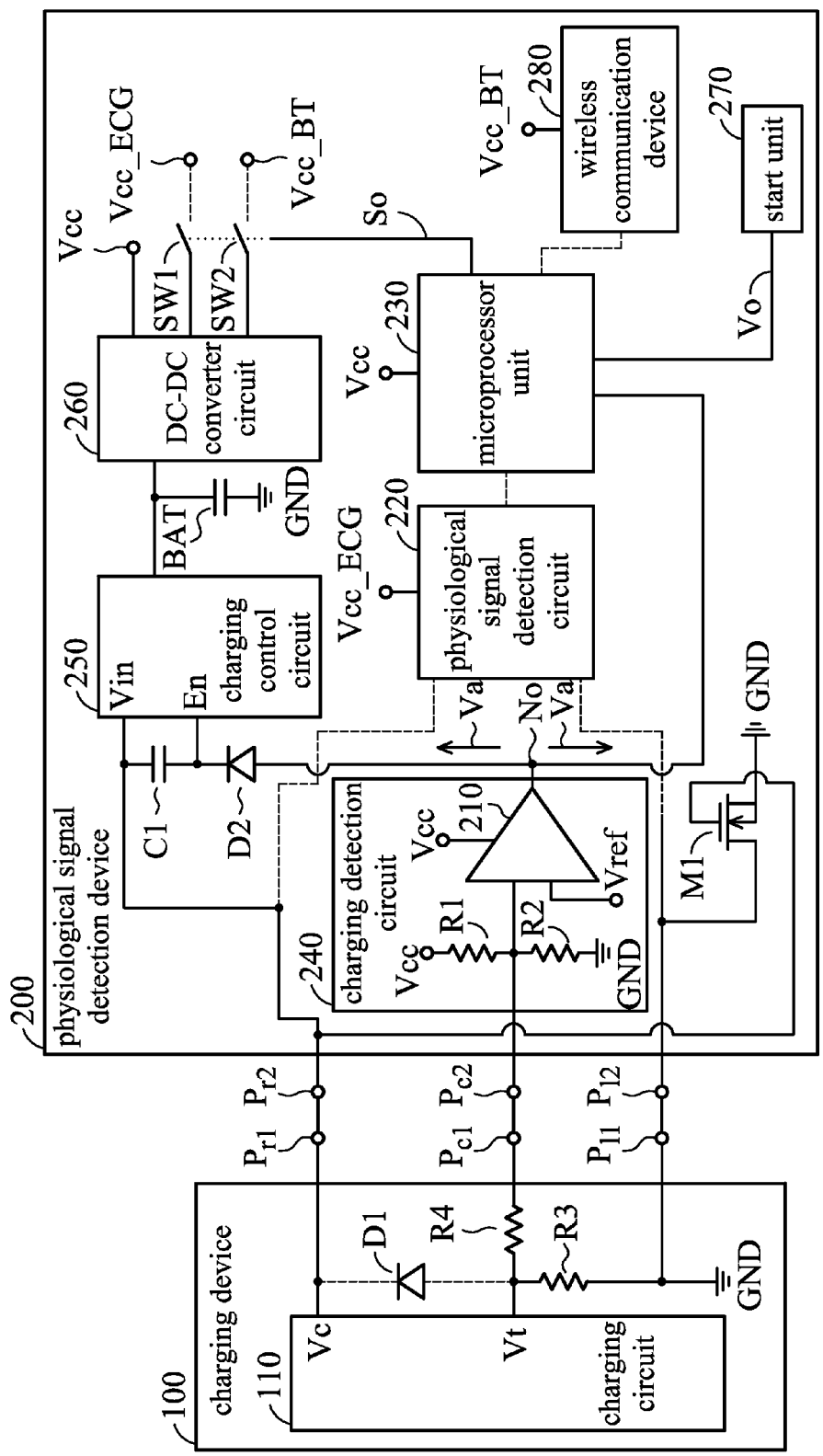
FIG. 3 is a circuit diagram for illustrating the embodiment, when the physiological signal detection device 200 is operating in the charging mode of FIG. 1.

FIG. 3 is a circuit diagram for illustrating the embodiment, when the physiological signal detection device 200 is operating in the charging mode of FIG. 1. The charging device 100 is connected with the physiological signal detection device 200 and the first output terminal $P_{r1}$, the second output terminal $P_{t1}$ and the charging indication terminal $P_{c1}$ are electrically connected to the first input terminal $P_{r2}$, the second input terminal $P_{t2}$ and the charging detection terminal $P_{c2}$. Because the charging indication terminal $P_{c1}$ inputs the charging indication signal Vt to the charging detection terminal $P_{c2}$, the voltage level of the charging detection terminal $P_{c2}$ is a second state (i.e. 3.0V). After the comparator 210 compares the voltage level of the charging detection terminal $P_{c2}$ with the reference voltage Vref (i.e. 2.8V), the charging detection circuit 240 outputs a corresponding first detection signal Va to the node No so as to correspondingly indicate the physiological signal detection device 200 operating in the charging/storage mode.

When the microprocessor unit 230 receives the first detection signal Va from the node No, the microprocessor unit 230 correspondingly generates a control signal So having the second voltage level so as to turn off the switch SW2 so that the power supply Vcc_BT does not be supplied to the wireless communication device 280 and turn off the switch SW1 so that the power supply Vcc_ECG does not be supplied to the physiological signal detection circuit 220. Under the charging mode, both of the wireless communication device 280 and the physiological signal detection circuit 220 stop working.

According to the first detection signal Va outputted from the node No, the charging control circuit 250 processes the power supply of the input terminal Vin and then provides the processed power supply to the battery BAT so that the charging device 100 inputs the voltage Vc to charge the battery BAT via the first output terminal $P_{r1}$ and the first input terminal $P_{r2}$. At the same time, because the transistor operates in the turn-on state, the second input terminal $P_{t2}$ is electrically connected to the negative terminal of the battery BAT and the ground. Therefore, the charging device 100 and the battery BAT form a loop to perform charging.

Figure 4:
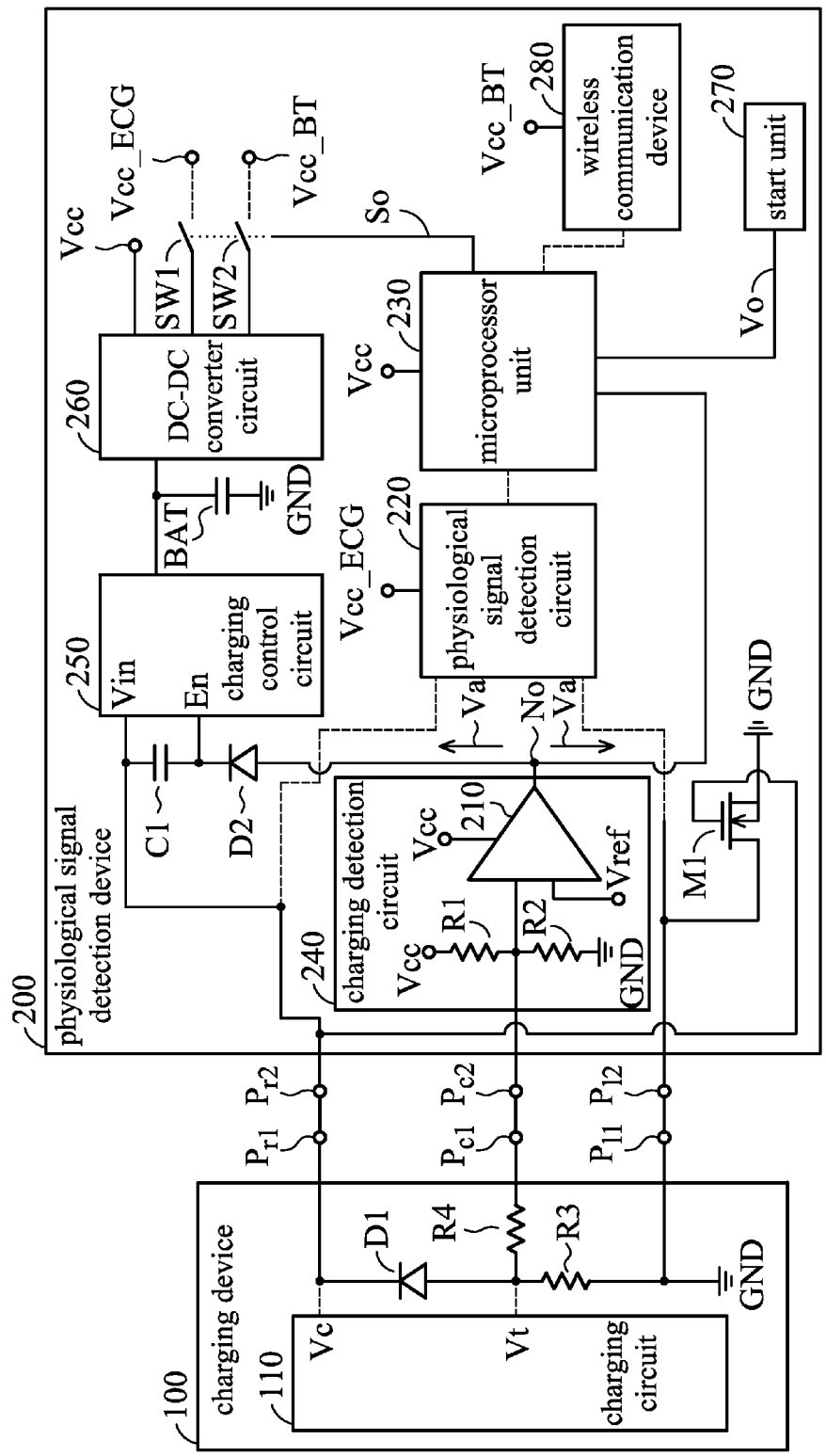
FIG. 4 is a circuit diagram for illustrating the embodiment, when the physiological signal detection device 200 is operating in the storage mode of FIG. 1.

FIG. 4 is a circuit diagram for illustrating the embodiment, when the physiological signal detection device 200 is operating in the storage mode of FIG. 1. Under the storage mode, the charging device 100 is connected with the physiological signal detection device 200, and the first output terminal $P_{r1}$, the second output terminal $P_{t1}$ and the charging indication terminal $P_{c1}$ are electrically connected to the first input terminal $P_{r2}$, the second input terminal $P_{t2}$ and the charging detection terminal $P_{c2}$ of the physiological signal detection device 200. At this time, for instance, the charging device 100 is not connected to the power supply or disabled, so the charging device 100 does not supply the voltage Vc and the charging indication signal Vt to the physiological signal detection device 200. However, the battery BAT of the physiological signal detection device 200 still keeps providing the power supply Vcc, so the loop composed of resistors R3 and R4 and the charging detection circuit 240 makes the voltage of the charging detection terminal $P_{c2}$ be a third state (i.e. 2.2V). After the comparator 210 compares the voltage level of the charging detection terminal $P_{c2}$ with the reference voltage Vref (i.e. 2.8V), the charging detection circuit 240 still outputs a first detection signal Va to the node No so as to correspondingly indicate the physiological signal detection device 200 operating in the charging/storage mode.

When the microprocessor unit 230 receives the first detection signal Va from the node No, the microprocessor unit 230 correspondingly generates a control signal So having the second voltage level so as to turn off the switch SW2 so that the power supply Vcc_BT does not be supplied to the wireless communication device 280 and turn off the switch SW1 so that the power supply Vcc_ECG does not be supplied to the physiological signal detection circuit 220. Under the storage mode, both of the wireless communication device 280 and the physiological signal detection circuit 220 stop working.

The charging circuit 110 does not provide the voltage Vc, so the charging device 100 is barely used to load the physiological signal detection device 200 for storage.

In the invention, the physiological signal detection device 200 collocates with the charging device 100, so that the same terminals are used for charging and measuring. The collocation simplifies the use of the physiological signal detection device 200, reduces volume and has the characteristic of storage.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A physiological signal detection device, comprising:
a battery, disposed in the physiological signal detection device, comprising a positive terminal and a negative terminal;
a first input terminal;
a second input terminal;
a charging detection terminal, for receiving a charging indication signal from a charging device;
a physiological signal detection circuit, electrically coupled to the first input terminal and the second input terminal, wherein, when the first input terminal and the second input terminal are electrically connected to a measure target, the physiological signal detection circuit generates a physiological signal according to a detection result of the first input terminal and the second input terminal; and
a charging control circuit, electrically coupled to the first input terminal, the second input terminal and the charging detection terminal, wherein, when the first input terminal and the second input terminal are coupled to a power supply supplied by the charging device, the charging detection terminal receives the charging indication signal of the charging device and according to the charging indication signal the charging control circuit is enabled so as to charge the battery with the power supply,
wherein:
the charging control circuit further comprises a first resistor coupling the charging detection terminal to a power terminal of the charging control circuit;
when the first input terminal, the second input terminal and the charging detection terminal are coupled to the charging device but the charging device is not supplying the power supply, the first resistor and internal resistors within the charging device and coupled to the charging detection terminal form a voltage divider that divides a voltage at the power terminal of the charging control circuit to generate a divided voltage at the charging detection terminal for recognizing that the physiological signal detection device is operated in a storage mode;
the charging control circuit further comprises a second resistor coupled between the charging detection terminal and a ground terminal;
the charging device comprises a third resistor and a fourth resistor to be coupled in series between the charging detection terminal and a ground terminal; and
the charging device further comprises a diode having an anode coupled to a connection node between the third resistor and the fourth resistor and having a cathode to be coupled to the first input terminal.

2. The physiological signal detection device as claimed in claim 1, further comprising:
a microprocessor unit, electrically coupled to the charging detection terminal and the physiological signal detection circuit, wherein the microprocessor unit receives the physiological signal generated from the physiological signal detection circuit and calculates a plurality of physiological information according to the physiological signal.

3. The physiological signal detection device as claimed in claim 2, further comprising:
a power switch, coupled to the microprocessor unit, the physiological signal detection circuit and the battery, wherein when the charging detection terminal receives the charging indication signal, the microprocessor unit responds to the charging indication signal to turn off the power switch so as to make the battery stop supplying power to the physiological signal detection circuit.

4. The physiological signal detection device as claimed in claim 3, further comprising:
a start unit, coupled to the microprocessor unit, wherein when the start unit transmits a start signal to the microprocessor unit, the physiological signal detection device is under a measuring operation mode and the microprocessor unit further turns on the power switch so as to make the battery supply power to the physiological signal detection circuit.

5. The physiological signal detection device as claimed in claim 4, wherein the start unit is a Hall sensor.

6. The physiological signal detection device as claimed in claim 2, further comprising:
a short range radio communication device, electrically coupled to the microprocessor unit, wherein the short range radio communication device receives and transforms the plurality of physiological information into a wireless signal.

7. The physiological signal detection device as claimed in claim 2, wherein the plurality of physiological information comprise heart rate, calorie consumption, electrocardiogram, and exercise time.

8. The physiological signal detection device as claimed in claim 1, further comprising:
a DC-DC converter circuit, coupled to the battery, wherein the DC-DC converter circuit transforms a voltage of the battery and supplies a transformed voltage to an inner circuit of the physiological signal detection device.

9. The physiological signal detection device as claimed in claim 1, further comprising the charging device, wherein the charging device comprises:
a first output terminal, a charging indication terminal, and a second output terminal respectively coupled to the first input terminal, the charging detection terminal and the second input terminal; and
a charging circuit, coupled to the first terminal, the second terminal and the third terminal so as to supply the power supply and the charging indication signal.

* * * * *